(12) United States Patent
Raulerson et al.

(10) Patent No.: US 7,220,246 B2
(45) Date of Patent: May 22, 2007

(54) CATHETER HUB CLIP

(75) Inventors: J. Daniel Raulerson, Brewton, AL (US); Mark Fisher, Sellersville, PA (US)

(73) Assignee: Medical Components, Inc., Harleysville, PA (US)

( * ) Notice: Subject to any disclaimer, the term of this patent is extended or adjusted under 35 U.S.C. 154(b) by 20 days.

(21) Appl. No.: 11/179,421

(22) Filed: Jul. 12, 2005

(65) Prior Publication Data

US 2006/0015072 A1  Jan. 19, 2006

Related U.S. Application Data

(60) Provisional application No. 60/587,981, filed on Jul. 14, 2004.

(51) Int. Cl.
*A61M 5/00* (2006.01)

(52) U.S. Cl. ..................................... 604/174
(58) Field of Classification Search ............ 604/174, 604/180; 128/DIG. 6, DIG. 26
See application file for complete search history.

(56) References Cited

U.S. PATENT DOCUMENTS

| | | | |
|---|---|---|---|
| 4,397,647 A * | 8/1983 | Gordon | ............ 604/180 |
| 4,645,492 A | 2/1987 | Weeks | |
| 4,650,474 A | 3/1987 | De Backer | |
| 4,699,616 A | 10/1987 | Nowak et al. | |
| 4,711,636 A | 12/1987 | Bierman | |
| 4,981,475 A | 1/1991 | Haindl | |
| 5,192,273 A | 3/1993 | Bierman et al. | |
| 5,192,274 A | 3/1993 | Bierman | |
| 5,224,935 A | 7/1993 | Hollands | |
| D347,060 S | 5/1994 | Bierman | |
| 5,314,411 A | 5/1994 | Bierman et al. | |
| 5,354,282 A | 10/1994 | Bierman | |
| 5,456,671 A | 10/1995 | Bierman | |
| D375,355 S | 11/1996 | Bierman | |
| 5,578,013 A | 11/1996 | Bierman | |
| 5,637,098 A | 6/1997 | Bierman | |
| 5,702,371 A | 12/1997 | Bierman | |
| 5,795,335 A * | 8/1998 | Zinreich | ............ 604/174 |

(Continued)

OTHER PUBLICATIONS

International Search REport dated Dec. 6, 2006, PCT/US05/24648 (3 pages).

(Continued)

*Primary Examiner*—LoAn H. Thanh
(74) *Attorney, Agent, or Firm*—Anton P Ness; Fox Rothschild LLP

(57) ABSTRACT

A clip (100) for retaining a catheter hub (160) to a patient. The clip includes a base (110) having a first surface (112) and a second surface (114) juxtaposed from the first surface. The clip also includes a first prong (122) extending from the first surface for retaining a first suture loop (162) of the catheter hub (160) to the base (110) and a second prong (142) extending from the first surface for retaining a second suture loop (164) of the catheter hub to the base. A method for clipping a catheter hub to a patient is also disclosed, wherein a clip base is secured to the patient, and a catheter hub is pressed onto the clip and locked to the clip by suture loops of the hub being locked by respective securing sections of the clip in a manner permitting unsecuring the hub from the clip for removal.

20 Claims, 3 Drawing Sheets

U.S. PATENT DOCUMENTS

| | | |
|---|---|---|
| 5,800,402 A | 9/1998 | Bierman |
| 5,810,781 A | 9/1998 | Bierman |
| 6,132,398 A | 10/2000 | Bierman |
| 6,213,979 B1 | 4/2001 | Bierman |
| 6,224,571 B1 | 5/2001 | Bierman |
| 6,290,676 B1 | 9/2001 | Bierman |
| 6,428,515 B1 | 8/2002 | Bierman et al. |
| 6,447,485 B2 * | 9/2002 | Bierman .................. 604/174 |
| 6,491,664 B2 * | 12/2002 | Bierman .................. 604/180 |
| 6,572,588 B1 | 6/2003 | Bierman |
| 6,979,320 B2 * | 12/2005 | Bierman .................. 604/180 |
| 2004/0097903 A1 * | 5/2004 | Raulerson .................. 604/523 |
| 2005/0038453 A1 | 2/2005 | Raulerson |

OTHER PUBLICATIONS

Written Opinion dated Dec. 6, 2006, PCT/US05/24648 (4 pages).

* cited by examiner

CATHETER HUB CLIP

CROSS-REFERENCE TO RELATED APPLICATION

This relates to and claims priority from Provisional U.S. Patent Application Ser. No. 60/587,981 filed Jul. 14, 2004.

FIELD OF THE INVENTION

The present invention relates to an apparatus for releasably retaining a catheter hub to the skin of a patient.

BACKGROUND OF THE INVENTION

Catheters are commonly used to insert and remove fluids, such as medication and/or blood to and from the bloodstream of a patient. A catheter typically includes a connection point, such as a hub, that remains exterior of the patient after the catheter is inserted into the patient, and is used to secure the catheter to the patient to reduce the likelihood of the catheter being accidentally dislodged from the patient.

After the catheter is installed, the catheter hub is typically fixedly connected to the patient's skin, such as by suturing the hub directly to the skin. To facilitate this suturing, the hub typically includes a pair of loops, or suture wings, that extend laterally from the hub through which sutures may be passed. The sutures secure the suture wings to the surface of the patient's skin, securing the hub to the patient and restricting the ability of the hub to move relative to the patient.

However, such suturing produces skin penetration that may lead to infection in the patient. Others have developed adhesive-based structures for securing a catheter to the external skin of the patient. See, for example, U.S. Pat. Nos. 5,192,274; 5,456,671; 5,637,098; 5,702,371; 6,491,664; and 6,572,588, that all disclose various configurations of securing a catheter or catheter hub on a base structure, with a face of the base structure incorporating an adhesive to secure the catheter to the patient's skin without piercing the skin, such as with sutures.

Certain catheters, such as the SPLIT STREAM® catheter sold by Medical Components, Inc. of Harleysville, Pennsylvania, include a catheter ingrowth cuff that is subcutaneously implanted during catheter insertion. A removable hub is connected to the catheter and is intended to remain connected to the catheter only until subcutaneous skin tissue has had time to grow into the cuff to secure the cuff and the catheter subcutaneously. After the cuff is subcutaneously secured, it is preferred to remove the hub from the catheter, to alleviate any patient discomfort that may be caused by the hub rubbing against the skin.

It would be beneficial to provide a securing device that would releasably retain the hub for a catheter against the patient's skin without the need for suturing the hub to the skin.

BRIEF SUMMARY OF THE PRESENT INVENTION

Briefly, the present invention provides a clip comprising a base having a first surface and a second surface juxtaposed from the first surface. The clip also includes a first section for retaining a catheter hub to the base, wherein the first section extends from the first surface and a second section for retaining the catheter hub to the base, wherein the second section extends from the first surface.

Additionally, the present invention also provides a method of releasably attaching a hub to a clip comprising providing a hub including a body disposed against the first surface of the base, a first loop disposed on a first side of the body, and a second loop disposed on a second side of the body. The method also includes providing a clip including a base having a first surface and a second surface juxtaposed from the first surface, a first section for retaining a catheter hub to the base, wherein the first section extends from the first surface, and a second section for retaining the catheter hub to the base, wherein the second section extends from the first surface. The method further includes disposing the first loop over the first section and disposing the second loop over the second section and urging the hub toward the first surface, thereby biasing at least a portion of the first section and at least a portion of the second section toward each other; and engaging the hub body against the first surface, thereby unbiasing at least the portion of the first section and at least the portion of the second section away from each other, retaining the first wing loop against the first section and retaining the second loop against the second section.

The present invention further provides a method of removing a hub from a clip comprising providing a clip including a base having a first surface and a second surface juxtaposed from the first surface, a first section for retaining a catheter hub to the base, wherein the first section extends from the first surface; and a second section for retaining the catheter hub to the base, wherein the second section extends from the first surface. The method also includes providing a hub including a body disposed against the first surface of the base, a first loop disposed on a first side of the body, wherein the first loop is disposed over the first section for retaining the catheter hub to the base, and a second loop disposed on a second side of the body, wherein the second loop is disposed over the second section for retaining the catheter hub to the base. The method further includes disposing at least a portion of the first section and at least a portion of the second section toward each other; and disposing the hub away from the first surface of the base.

The present invention also provides a clip for retaining a catheter hub against a surface. The clip comprises a base, a first plane bisecting the base; and a first hub clip extending from the base on a first side of the plane. The first hub clip comprises a first prong, a first locator pin disposed on a first side of the first prong and a second locator pin disposed on a second side of the first prong. The clip also comprises a second hub clip extending from the base on a second side of the plane. The second hub clip is a mirror image of the first hub clip across the plane.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE PRESENT INVENTION

Figure 1:
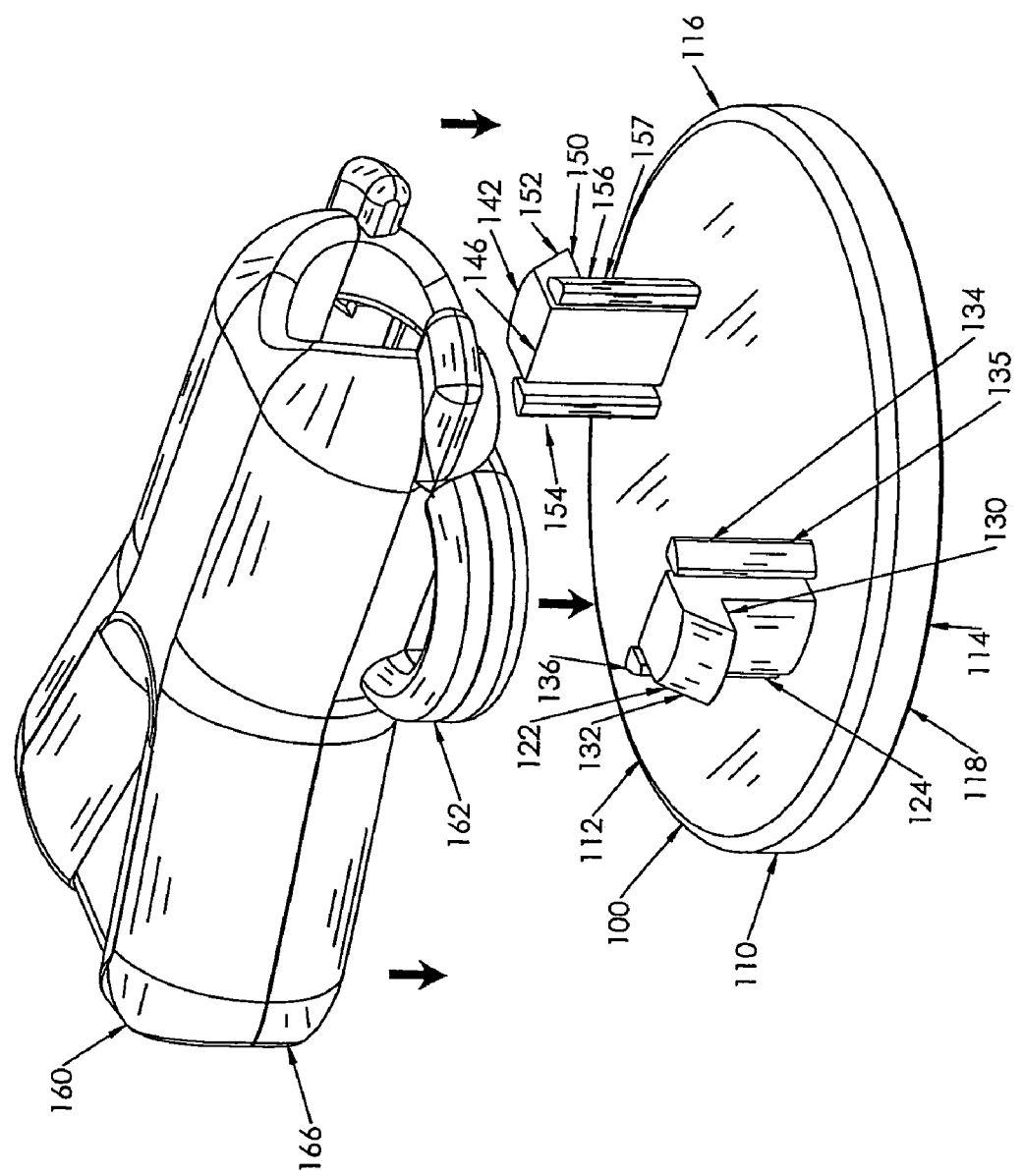
FIG. 1 is a perspective view of a catheter clip 100 according to the present invention, with a catheter hub being inserted onto the clip.

In the drawings, like numerals indicate like elements throughout. Certain terminology is used herein for convenience only and is not to be taken as a limitation on the present invention. The terminology includes words specifically mentioned, derivatives thereof, and words of similar import. The following describes a preferred embodiment of the invention. However, it should be understood based on this disclosure, that the invention is not limited by the preferred embodiment described herein.

A clip 100 for use in retaining a catheter hub 160 against a surface, such as the skin of a catheterized patient, is shown in perspective in FIG. 1. Preferably, the catheter hub 160 is the hub disclosed in U.S. Patent Publication No., US 2004/0097903, as well as in U.S. Patent Publication No. US 2004/0092863, the inventions of both of which are owned by the Assignee of the present invention and are incorporated herein by reference in their entireties.

Preferably, the clip 100 is constructed from a polymer such as polypropylene, or some other suitable material known to those skilled in the art. The material from which the clip 100 is constructed is preferably sufficiently flexible to allow portions of the clip 100 to flex when biased by an outside force, but to return generally toward or to an original position when the outside force is removed, as will be explained in more detail later herein.

The clip 100 includes a generally planar base 110 having a first surface 112 and a second surface 114 juxtaposed from the first surface 112. The base 110 is preferably generally circular in shape, although those skilled in the art will recognize that the base 110 may be other shapes as well. The first surface 112 may have a beveled edge 116, as shown in FIG. 1, although those skilled in the art will recognize that the edge 116 need not be beveled. The second surface 114 preferably includes a self-adhesive material 118, which is suitable for adhering a retaining device to the skin of a patient without sutures.

Figure 2:
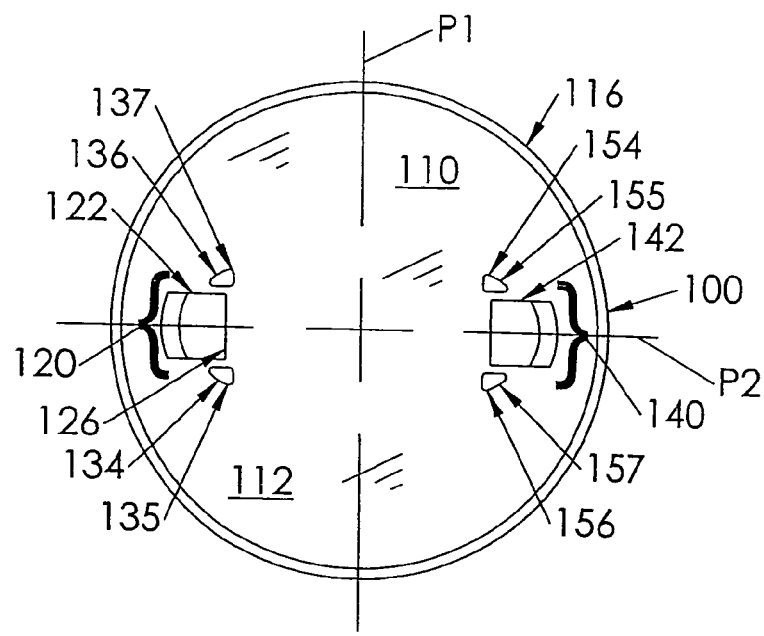
FIG. 2 is a top plan view of the catheter clip of FIG. 1.
Figure 2A:
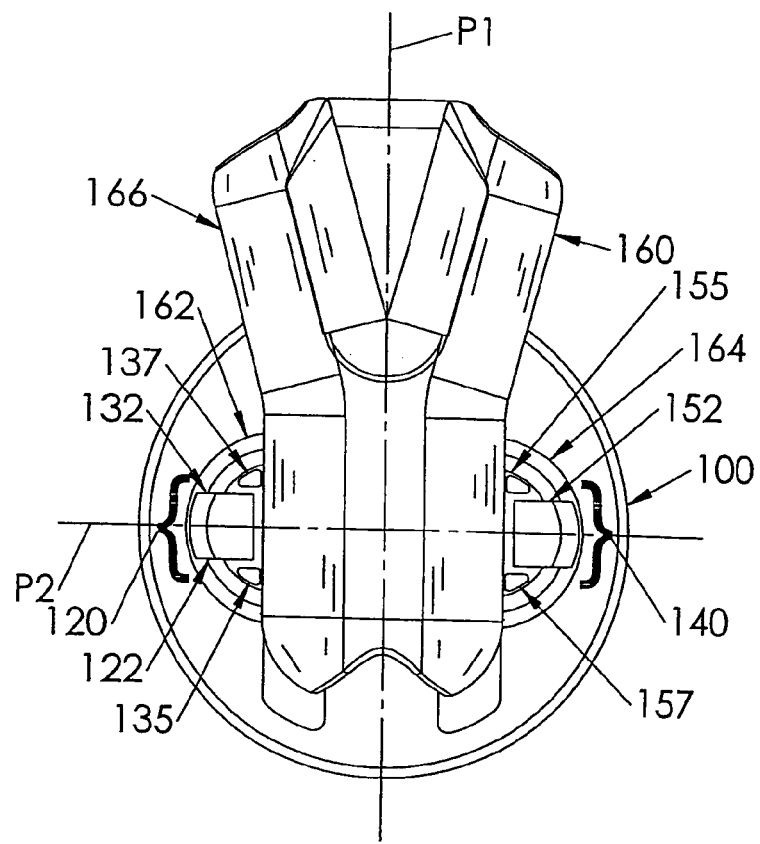
FIG. 2A, is a top plan view of the catheter clip of FIG. 1, with a catheter hub inserted onto the clip.

A planar view of the clip 100 is shown in FIG. 2 and a planar view of the clip 100 with the hub 160 inserted thereon is shown in FIG. 2A. The base 110 is shown to be bisected by a first plane P1, which is perpendicular to the base 110, and a second plane P2 that is perpendicular to the plane P1. A first retaining section 120 is disposed on one side of the plane P1, while a second retaining section 140 is disposed across plane P1, preferably as a mirror image of the first retaining section 120 across the plane P1. A sectional view of the clip 100 taken along plane P1 is shown in FIG. 3, while a sectional view of the clip 100 taken along plane P2 is shown in FIG. 4.

Figure 3:
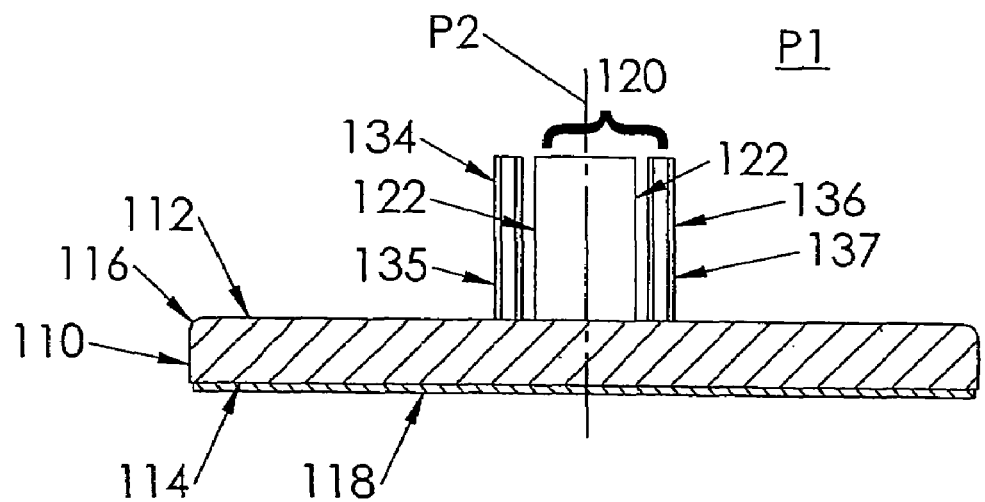
FIG. 3 is a sectional view of the clip of FIG. 1.
Figure 4:
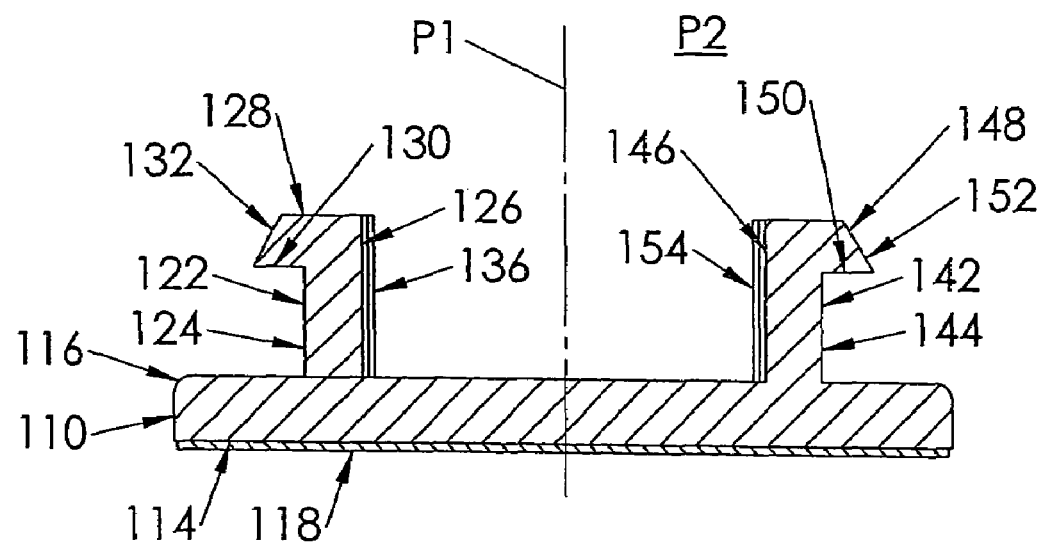
FIG. 4 is a sectional view of the clip of FIG. 1, taken along a line perpendicular to the section of FIG. 3.

Referring to FIGS. 1–4, the first retaining section 120 includes a first prong 122 that extends from the first surface 112, generally perpendicular to the first surface 112. The first prong 122 includes a generally arcuate outer face 124 with a convex curvature. As shown in FIG. 3, the plane P2 bisects the first prong 122. An inner face 126, juxtaposed from the outer face 124, may be generally flat and parallel to the plane P1, although those skilled in the art will recognize that the inner face 126 need not be generally flat and need not be parallel to the plane P1. A free end portion 128 of the first prong 122 includes a first lip 130 that extends from the outer face 124 and away from the first plane P1, generally parallel to the base 110. A beveled face 132 extends from the farthest edge of the first lip 130 toward the first plane P1 and away from the base 110. The beveled face 132 is preferably arcuate, with a convex curvature, although those skilled in the art will recognize that the beveled face 132 need not be arcuate.

Referring now to FIG. 3, but still in reference to the first retaining section 120, a first locator pin 134 is disposed adjacent the first prong 122 on one side of the second plane P2 and a second locator pin 136 is disposed adjacent the first prong 122 on the opposing side of the second plane P2. Preferably, the first and second locator pins 134, 136 are mirror images of each other across the second plane P2. Also preferably, an outside surface 135 of the first locator pin 134 is disposed distal from the first prong 122 and an outer surface 137 of the second pin 136 is disposed distal from the first prong 122.

The second retaining section 140 is preferably a mirror image of the first retaining section 120 across both the first plane P1 and the second plane P2. The second retaining section 140 includes a second prong 142 that extends from the first surface 112, generally perpendicular to the first surface 112. The second prong 142 includes a generally arcuate outer face 144 with a convex curvature. The plane P2 bisects the second prong 142. An inner face 146, juxtaposed from the outer face 144, may be generally flat and parallel to the plane P1, although those skilled in the art will recognize that the inner face 146 need not be generally flat and need not be parallel to the plane P1. A free end portion 148 of the second prong 142 includes a second lip 150 that extends from the outer face 144 and away from the first plane P1, generally parallel to the base 110. A beveled face 152 extends from the farthest edge of the second lip 150 toward the first plane P1 and away from the base 110. The beveled face 152 is preferably arcuate, with a convex curvature, although those skilled in the art will recognize that the beveled face 152 need not be arcuate.

A first locator pin 154 is disposed adjacent the second prong 142 on one side of the second plane P2 and a second locator pin 156 is disposed adjacent the second prong 142 on the opposing side of the second plane P2. Preferably, the first and second locator pins 154, 156 are mirror images of each other across the second plane P2. Also preferably, an outside surface 155 of the first locator pin 154 is disposed distal from the second prong 142 and an outer surface 157 of the second pin 156 is disposed distal from the second prong 142.

Referring back to FIG. 2A, the hub 160 is inserted onto the clip 100 so that a suture loop 162, 164 on either side of the hub 160 engages the first and second retaining section 120, 140, respectively, and the first and second retaining sections 120, 140 serve to releasably secure the hub 160 to the clip 100. As can be seen from FIG. 2A, each suture loop 162, 164 is generally semi-annular in shape, with an arcuate portion extending away from the body 166 of the hub 160. The first retaining section 120 is sized and spaced to fit in the first opening between the arcuate portion of the first suture loop 162 and the body 166, while the second retaining section 140 is sized and spaced to fit in the second opening between the arcuate portion of the second suture loop 164 and the body 166.

In operation, after a catheter (not shown) is inserted into a patient, the hub 160 is removably and longitudinally translatably secured to the catheter. The hub 160 is generally centered over the clip 100 so that a longitudinal plane of the hub 160 is generally co-planar with the first plane P1. The hub 160 and the clip 100 are then brought together so that the first suture loop 162 engages the beveled face 132 of the first prong 122 and the second suture loop 164 engages the beveled face 152 of the second prong 142. As the hub 160 is pressed against the clip 100, the force of each suture loop 162, 164 against each respective beveled face 132, 152 biases each of the first and second prongs 122, 142 toward the first plane P1.

After the first suture loop 162 has cleared the beveled face 132 of the first prong 122, the biasing force against the first prong 122 is released, and the first prong 122 snaps back toward its original, pre-biased position, and the first suture loop 162 is retained against the clip 100 by the first lip 130. The preferably arcuate outer face 124 preferably biases against the inner arcuate wall of the first suture loop 162 to firmly retain the first suture loop 162 against the first prong 122.

As the first suture loop 162 is being forced down over the first prong 122, the inner arcuate wall of the first suture loop 162, proximate to the hub body 166, is being disposed around the outside surfaces 135, 137 of the first and second locator pins 134, 136, respectively. The first suture loop 162 may bias each of the first and second locator pins 134, 136 toward the second plane P2, so that the first and second locator pins 134, 136 exert a reactive biasing force against the first suture loop 162 to firmly engage the first suture loop 162. The first and second locator pins 134, 136 restrict the hub 160 from longitudinally translating along an axis of the first plane P1, thus retaining the hub 160 securely against the clip 100.

Likewise, after the second suture loop 164 has cleared the beveled face 152 of the second prong 142, the biasing force against the second prong 142 is released, and the second prong 142 snaps back toward its original, pre-biased position, and the second suture loop 164 is retained against the clip 100 by the second lip 150. The preferably arcuate outer face 144 preferably biases against the inner arcuate wall of the second suture loop 164 to firmly retain the second suture wing loop 164 against the second prong 142.

As the second suture loop 164 is being forced down over the second prong 142, the inner arcuate wall of the second suture loop 164, proximate to the hub body 166, is being disposed around the outside surfaces 155, 157 of the first and second locator pins 154, 156, respectively. The second suture loop 164 may bias each of the first and second locator pins 154, 156 toward the second plane P2, so that the first and second locator pins 154, 156 exert a reactive biasing force against the second suture loop 164 to firmly engage the second suture loop 164. The first and second locator pins 154, 156 restrict the hub 160 from longitudinally translating along an axis of the first plane P1, thus retaining the hub 160 securely against the clip 100.

As shown in FIG. 2A, the hub 160 is now securely connected to the clip 100, with restricted ability of the hub 160 to translate along axes of either plane P1 or P2.

In the event that it is desired to remove the hub 160 from either the patient or the catheter, the beveled faces 132, 152 of each of the first and second prongs 122, 142, respectively, protrude above the first and second suture loops 162, 164 to be accessible for manual engagement, and are biased toward the first plane P1 until each respective lip 130, 150 clears its respective suture loop 162, 164. The hub 160 is then lifted away from the first surface 112 of the base 110, over the first and second prongs 120, 140, respectively, and away from the clip 100.

The hub 160 may now be removed from the catheter. If desired, the clip 100 may be removed from the patient by peeling the second surface 114 of the clip 100 from the patient's skin. The hub 160 may be repositioned at a new location along the length of the catheter, if desired. The clip 100 may thusly be relocated to a different position on the patient's skin and the hub 160 may be reconnected to the clip 100 as described above; if the hub 160 is no longer to be used, the clip 100 may be discarded.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A clip comprising:
   a base having a first surface and a second surface juxtaposed from the first surface;
   a first section for retaining a catheter hub to the base, wherein the first section extends from the first surface; and
   a second section for retaining the catheter hub to the base, wherein the second section extends from the first surface,
   wherein the first and second sections include respectively first and second prongs having at least portions thereof that are adapted to be biasable in opposite directions with respect to each other by portions of the catheter hub during assembly of the catheter hub to the clip,
   wherein the first section further comprises at least one locator pin adjacent to and separate from the first prong and
   wherein the first and second sections are sufficient to maintain the catheter hub clipped to the clip.

2. The clip according to claim 1, wherein the second surface comprises an adhesive.

3. The clip according to claim 1, further comprising a first plane generally bisecting the base, wherein the first section is disposed on a first side of the plane and the second section is disposed on an opposite side of the plane.

4. A method of releasably attaching a hub to a clip comprising:
   providing a clip including:
      a base having a first surface and a second surface juxtaposed from the first surface;
      a first section for retaining a catheter hub to the base, wherein the first section extends from the first surface and wherein the first section comprises a first prong and at least one locator pin adjacent to and separate from the first prong; and
      a second section for retaining the catheter hub to the base, wherein the second section extends from the first surface;
   providing a hub including:
      a body disposed against the first surface of the base of the clip;
      a first loop disposed on a first side of the body; and
      a second loop disposed on a second side of the body;
   disposing the first loop of the hub over the first section of the clip and disposing the second loop of the hub over the second section of the clip;
   urging the hub toward the base, thereby biasing at least a portion of the first section and at least a portion of the second section toward each other; and
   engaging the hub body against the first surface of the clip, thereby unbiasing at least the portion of the first section and at least the portion of the second section away from each other, retaining the first loop against the first section and retaining the second loop against the second section.

5. A method of removing a hub from a clip comprising:
   providing a clip including:

a base having a first surface and a second surface juxtaposed from the first surface;

a first section for retaining a catheter hub to the base, wherein the first section extends from the first surface and wherein the first section comprises a first prong and at least one locator pin adjacent to and separate from the first prong; and a second section for retaining the catheter hub to the base, wherein the second section extends from the first surface;

providing a hub including:

a body disposed against the first surface of the base;

a first loop disposed on a first side of the body, wherein the first loop is disposed over the first section for retaining the catheter hub to the base; and a second loop disposed on a second side of the body, wherein the second loop is disposed over the second section for retaining the catheter hub to the base;

disposing at least a portion of the first section and at least a portion of the second section toward each other whereafter the catheter hub is removable from the clip; and disposing the hub away from the first surface of the base.

6. The method according to claim 5, further comprising, after removing the hub from the clip, discarding the hub.

7. The method according to claim 5, further comprising, after removing the hub from the clip, discarding the clip.

8. A clip for retaining a catheter hub against a surface comprising:

a base;

a first plane bisecting the base;

a first hub clip extending from the base on a first side of the plane, wherein the first hub clip comprises a first prong, a first locator pin disposed adjacent to a first side of the first prong and a second locator pin disposed adjacent to a second side of the first prong; and a second hub clip extending from the base on a second side of the plane, wherein the second hub clip is a mirror image of the first hub clip across the plane, wherein the first and second hub clips are sufficient to maintain the catheter hub clipped to the clip.

9. The clip according to claim 8, further comprising a second plane bisecting the base, wherein the second plane extends perpendicularly to the first plane, and wherein the clip is symmetric about the second plane.

10. The clip according to claim 8, wherein the first prong is able to be biased toward the first plane.

11. The clip according to claim 8, wherein the clip is symmetric about the first plane.

12. The clip according to claim 8, wherein the first prong comprises a first lip extending away from the first plane.

13. The clip according to claim 8, wherein the second hub clip comprises a second prong extending from the base.

14. The clip according to claim 13, wherein the second prong comprises a second lip extending away from the first plane.

15. The clip according to claim 1, wherein a pair of locator pins are disposed adjacent to and separate from the first prong.

16. The clip according to claim 1, wherein the second section comprises a second prong and at least one locator pin adjacent to and separate from the second prong.

17. The clip according to claim 1, wherein a pair of locator pins are disposed adjacent to and separate from the second prong.

18. The clip according to claim 1, wherein the first and second prongs have at least portions thereof that are adapted to be engaged to be biasable toward each other.

19. The clip according to claim 8, wherein the first and second prongs have at least portions thereof that are adapted to be engaged to be biasable in opposite directions with respect to each other.

20. A combination of a catheter hub and a retaining clip, for securing a catheter assembly to a patient, comprising:

a catheter hub having a hub body having opposite sides and including a bottom surface, and further having first and second loops extending from the opposite sides defining respective first and second openings between the loops and the respective hub body sides; and a clip having a base securable to a patient without sutures; the clip further having first and second clip sections coextending upwardly from the base to free ends, the first and second clip sections associated with the first and second loops and the respective first and second openings, the clip further comprises a first prong and at least one locator pin adjacent to and separate from the first prong wherein the free ends of the first and second clip sections are sized to be received through the respective openings when inserting the catheter onto the clip, wherein the free ends include respective lips that are sized to overlie the first and second loops when the catheter hub is urged against the clip base, and wherein the first and second clip sections are biasable toward each other upon engagement by the first and second loops when the catheter hub is urged toward the clip base and become unbiased when the bottom of the catheter hub is adjacent to the clip base.

* * * * *